(12) United States Patent
Moissl et al.

(10) Patent No.: US 8,583,226 B2
(45) Date of Patent: Nov. 12, 2013

(54) METHOD FOR DETERMINING A CORRECTED VOLUME COMPARTMENT OF AN AMPUTATED PATIENT, DEVICE FOR CARRYING OUT THE METHOD AND COMPUTER PROGRAM PRODUCT

(75) Inventors: Ulrich Moissl, Bad Vilbel (DE); Peter Wabel, Darmstadt (DE); Sebastian Wieskotten, Ober-Ramstadt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 219 days.

(21) Appl. No.: 13/121,039

(22) PCT Filed: Oct. 14, 2009

(86) PCT No.: PCT/EP2009/007366
§ 371 (c)(1),
(2), (4) Date: Mar. 25, 2011

(87) PCT Pub. No.: WO2010/043381
PCT Pub. Date: Apr. 22, 2010

(65) Prior Publication Data
US 2011/0184309 A1 Jul. 28, 2011

(30) Foreign Application Priority Data
Oct. 15, 2008 (DE) .......................... 10 2008 051 347

(51) Int. Cl.
*A61B 5/05* (2006.01)
(52) U.S. Cl.
USPC ........................................................ 600/547
(58) Field of Classification Search
USPC ........................................................ 600/547
See application file for complete search history.

(56) References Cited

U.S. PATENT DOCUMENTS

2009/0131812 A1* 5/2009 Sato et al. .................... 600/547

FOREIGN PATENT DOCUMENTS

| WO | WO 2006/002656 A1 | 1/2006 |
| WO | WO 2006/002685 | 1/2006 |

OTHER PUBLICATIONS

Rottmann, et al., "Bestimmung der Koerperzusammensetzung mittels Bioimpedanzspektroskopie unter Beruecksichtigung von Amputationen," Diplomarbeit, pp. 1-69, May, 2007, XP0091133889—(English translation of p. 6, paragraph 2 to p. 7, paragraph 1; p. 19, paragraph 1 to p. 37, paragraph 3; p. 56, paragraph 5 to p. 65, paragraph 3.).

Wieskotten, S., et al., "Konzeptentwurf fuer eine Modell-basierte Bestimmung von Koerperzusammensetzung and Ueberwaesserung bei Dialysepatienten mt Amputationen," Automatisierungstechnische Verfahren Fur Die Medizin: 7, Workshop; Tagungsband, pp. 21-22, Jan. 2007, XP00913376—(English translation of pp. 21-22.).

* cited by examiner

*Primary Examiner* — Rene Towa
(74) *Attorney, Agent, or Firm* — Jacobson Holman PLLC

(57) ABSTRACT

The invention relates to the field of monitoring the hydration- and/or nutrition status of a patient by means of bioimpedance measurement values. This is based on the problem of also being able to determine by such measurements the body composition of an amputated person simply and individually. The invention is based on the observation that volume compartments can also be determined in amputated patients by means of bioimpedance measurements when reference is made to the body models, used and established hitherto for patients without amputations, without major adaptation. Merely the determining of a characteristic factor for the amputation is necessary, which can be determined by comparative measurements in advance. In particular exceptional situations of multiple amputations, it can be indicated to submit additional parameters to increase accuracy. Then the body models hitherto can also be further used for these cases.

18 Claims, 3 Drawing Sheets

Figure 1:
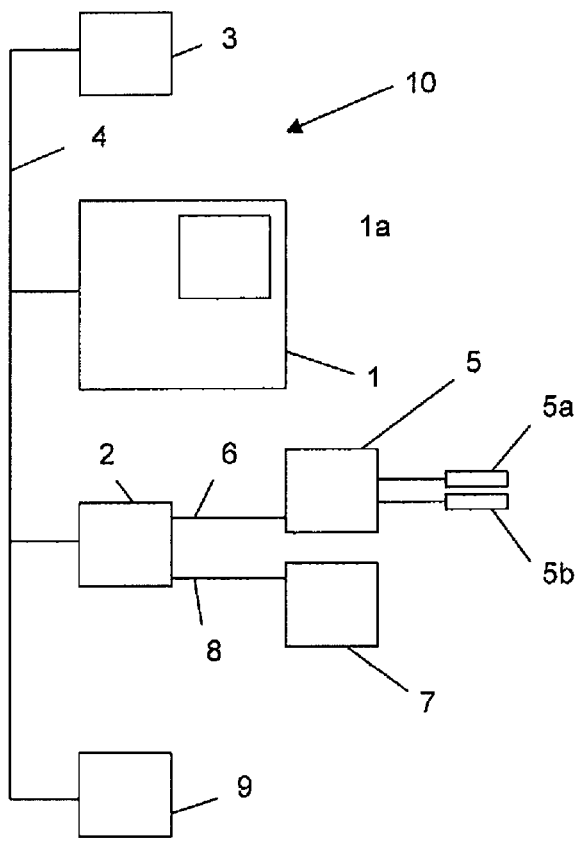

Amputation beider Arme
(a)
Amputation of both arms

Amputation beider Beine
(b)
Amputation of both legs

| Normal Measurement | Amputation Arm | Amputation Leg leg | Amputation Arm + Leg |
|---|---|---|---|
| (a) | (b) | (c) | (d) |

Amputation beider Arme  Amputation beider Beine
(a) (b)
Amputation of both arms  Amputation of both legs Percentage of body weight   Left Side   Right Side
Complete arm      6.6%
Above elbow       3.1%
Below elbow       1.5%
Complete leg     18.5%
Above knee        8.0%
Below knee        6.5%
Total of all percentages:

|  | ECW | ICW | LTM | ATM | OH |
|---|---|---|---|---|---|
| $m_{FF}$ | 0,89 | 0,91 | 0.90 | 0,97 | 0,68 |
| $o_{FF}$ | 0,69 | -0,49 | -1,03 | 3,73 | -0,22 |
| $m_{HH}$ | 0,85 | 0,81 | 0,78 | 0,85 | 1,00 |
| $o_{HH}$ | 1,19 | 3,46 | 9,31 | 2,49 | -0,33 |

Fig. 5

METHOD FOR DETERMINING A CORRECTED VOLUME COMPARTMENT OF AN AMPUTATED PATIENT, DEVICE FOR CARRYING OUT THE METHOD AND COMPUTER PROGRAM PRODUCT

This is a national stage of PCT/EP09/007366 filed Oct. 14, 2009 and published in German, which claims the priority of German number 10 2008 051 347.4 filed Oct. 15, 2008, hereby incorporated by reference.

The invention relates to the field of monitoring the hydration- and/or nutritional status of a patient by means of bioimpedance measurement values.

The kidneys have several functions in order to maintain the healthy status of a human body. Firstly, they control the fluid balance by the separation of any excess fluid from the blood volume of the patient. Secondly, they serve to purify the blood of any waste products such as urea and creatinine. Last but not least, they also control the level of particular substances in the blood, such as electrolytes, in order to ensure a healthy and necessary concentration level.

In the case of a kidney failure, fluid which has been taken in accumulates in the body tissue and causes increasing stress on the blood circulation or the vascular system. This excess of fluid must be removed from the blood during a dialysis treatment by ultrafiltration. When an insufficient quantity of fluid is removed, the long-term consequences can be serious and can lead to high blood pressure and heart failure. The likelihood of the occurrence of heart failure is distinctly increased in dialysis patients, and it is assumed that the conditions of a fluid overload is one of the decisive factors. A removal of too much fluid is likewise dangerous, because the dialysis patient becomes dehydrated and this leads to hypotension.

The dry weight (for simplicity, the words "weight" and "mass" are to be used synonymously within the framework of this patent application—which corresponds to usual practice in the medical field) defines the weight of a patient, which would be reached when the kidneys are working normally. In other words, it represents the optimum target weight (or the fluid status) which is to be reached in order to minimize the cardiovascular risk. The dry weight was always a difficult problem to grasp in general clinical practice, because there is a lack of quantitative methods to determine it. Currently, the dry weight problem is approached using indirect indicators such as, for example, blood pressure, echocardiographic examinations and subjective information such as X-ray photographs. Furthermore, it was extremely difficult to define a compilation of conditions which are generally accepted as a dry weight standard.

A promising method for deriving the fluid status of a patient involves the use of bioimpedance measurements. A low alternating current is applied via two or more electrodes which are attached to the patient and the corresponding electric potential difference is measured. The various fluid compartments of the human body contribute differently to the measured signal. The use of multiple frequencies allows the intracellular water volume (ICV) and the extracellular water volume (ECV) to be determined. With this data, it is possible to determine the hydration status in the sense of an excess of fluid or a dehydration. An example of such a device is described in the international patent application WO 2006/002685. With such a device, it is possible at the same time to determine the body composition with respect to other volume compartments of the patient, in particular the proportion of lean and adipose tissue. In this way, conclusions are also possible with regard to the nutrition status of the patient.

The models forming the basis of the evaluation of bioimpedance measurements have in common the fact that they either originate from the body of a patient who is not lacking any extremities or members, or instead of a whole body measurement are restricted only to a segmental measurement on a particular body segment.

In this connection, the question is raised as to how a whole body measurement can be carried out to determine the body composition in amputated patients who are lacking individual members or parts thereof. Amputations of extremities are to be found more frequently in a dialysis population than in the normal population. The cause of this is generally diabetes. A blood sugar level which is too high damages the fine capillary networks of the body, in particular in the kidneys and the extremities. Possible consequences of diabetes are kidney failure and the amputation of extremities.

By means of a so-called 4-point measurement, experiments have been carried out to determine the segmental proportions of the body of healthy subjects and on this basis to investigate the influence of amputations (Wieskotten et. al, in: Tagungsband Automatisierungstechnische Verfahren für die Medizin—7. Workshop 2007, ISBN 978-3-18-326717-0)).

The invention is based on the problem of providing a method by which the body composition of an amputated patient can be determined simply and individually by means of bioimpedance measurements. The invention is also based on the problem of providing a device for such a bioimpedance measurement for determining the body composition of an amputated patient. The invention also relates to a computer program product to carry out the method according to the invention.

According to the teaching of the invention, these problems are solved by a method for determining a corrected volume compartment $V(t)$ of a patient at the time t, where the patient is missing individual members or parts thereof, comprising the following steps: bioimpedance data on the patient is measured at time t, a volume compartment $V'(t)$ of the patient is determined by means of the measured bioimpedance data, and the corrected volume compartment $V(t)$ is determined by multiplication of the volume compartment $V'(t)$ or of a value correlated therewith with a characteristic factor k for the missing member or parts thereof, by a device with a bioimpedance measurement arrangement for the measurement of bioimpedance data on the patient, an evaluation unit which is configured so that by means of the measured bioimpedance data a volume compartment $V'(t)$ of the patient is determined and the corrected volume compartment $V(t)$ is determined by multiplication of the volume compartment $V'(t)$ or of a value correlated therewith with a factor k which is characteristic for the missing member or parts thereof; and by a computer program product with a memory carrier with a stored computer program to carry out the method. Advantageous developments are the subject of the sub-claims.

The invention is based on the knowledge that to take into consideration missing members or extremities for determining the body composition, no adapted patient models are required at all, but rather firstly one can proceed from the original body model which is used for the case where a patient has no members or parts thereof missing. Body composition is understood to mean in this sense a partial component of the human body which can be indicated as a volume compartment, whether it is in a volume- or mass unit, absolutely or relatively.

According to the method according to the invention, a corrected volume compartment $V(t)$ of a patient can be determined at the time t, with individual members or parts thereof missing from the patient, by firstly bioimpedance data being measured on the patient, then a volume compartment V'(t) being determined and subsequently the corrected volume compartment V(t) being obtained by multiplication of the volume compartment V'(t) or of a value correlated therewith with a factor k characteristic for the missing member or parts thereof.

The volume compartments can, for example, comprise lean tissue (LTM), adipose tissue (ATM), overwatering volume (OH), extracellular water (ECW), intracellular water (ICW) or can be selected from these parameters.

In a preferred embodiment, the bioimpedance measurement is carried out as a whole body measurement. A whole body measurement is understood in this context to mean a measurement in which the electric current penetrates several body segments which comprise at least the torso. In the absence of an arm or parts thereof and/or in the absence of a leg or parts thereof, the whole body measurement can be carried out with voltage- and current electrodes which are attached in the vicinity of an existing wrist and in the vicinity of an existing ankle. If both legs or parts thereof are missing, the voltage- and current electrodes can be attached in the vicinity of both wrists, and in the vicinity of both ankles if both arms or parts thereof are missing.

In a further embodiment, the correction factor k is determined on the basis of comparative data, in which the proportion of the missing member or of a part thereof is determined on the basis of its proportion to the total weight of a comparative patient without missing members or parts thereof.

In a particularly simple application of the method according to the invention, the body weight M(t) of the patient is calculated and with the determining of the volume compartment V'(t) a corrected body weight M'(t) is used, which is produced from the quotient of the measured body weight M(t) divided by the correction factor k. In this way, the evaluation of the measurement values takes place as if they were undertaken on patients without amputated members. After the determining of the volume compartment V'(t), the circumstance must be allowed for that the volume compartment has to be corrected proportionately by the member which is not present, which is carried out successfully according to the invention by multiplication with the correction factor k.

The device according to the invention is constructed to carry out the method according to the invention. It comprises a bioimpedance measurement arrangement for the measurement of bioimpedance data on the patient and an evaluation unit, which is configured so that by means of the measured bioimpedance data a volume compartment V'(t) of the patient is determined and the corrected volume compartment V(t) is determined by multiplication of the volume compartment V'(t) or a value correlated therewith with a factor k which is characteristic for the missing member or parts thereof.

By means of the computer program product according to the invention, a device which comprises a bioimpedance measurement arrangement and a programmable evaluation unit can be configured according to the invention by transmission of the program, which is stored on the computer program product, into the evaluation unit, whereby it is made possible to carry out the method according to the invention.

Figure 2:
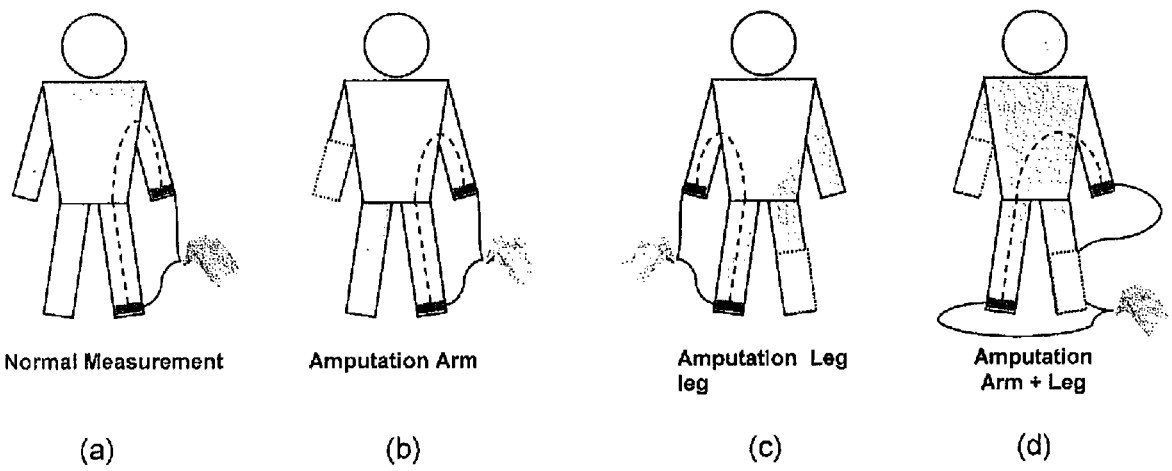

Further details and advantages of the invention are described in further detail with the aid of an example embodiment, illustrated in the drawings, showing:

FIG. 1 an embodiment of a device for determining a corrected volume compartment V(t) of a patient at the time t, with individual members or parts thereof missing from the patient, in diagrammatic form, FIG. 2 the arrangement of the bioimpedance electrodes for whole body bioimpedance measurement in the case of missing members or extremities: (a) for comparison without missing members, (b) in the case of one missing arm, (c) in the case of one missing leg and (d) in the case of one missing arm and one missing leg FIG. 3 the arrangement of the bioimpedance electrodes for whole body bioimpedance measurement in the case of missing members or extremities: (a) in the case of both arms missing and (b) in the case of both legs missing, FIG. 4 a table to determine the correction factor k and FIG. 5 example data for additional parameter values for evaluation in the case of the arrangements shown in FIG. 3.

FIG. 1 shows an embodiment of the device 10 according to the invention. Such an embodiment of a device to determine a corrected volume compartment V(t) of a patient, where individual members or parts thereof are missing from the patient, comprises an evaluation unit 1 constructed as a microprocessor unit, which in turn comprises a microprocessor program memory unit 1a. The evaluation unit 1 is connected via connecting means 4 with an input unit 2 and a memory unit 3. A program for determining a corrected volume compartment V(t) of a patient at the time t, where individual members or parts thereof are missing from the patient, is stored in the microprocessor program memory unit 1a.

To determine bioimpedance measurement data, a bioimpedance measurement arrangement 5 is provided, which is connected via a connection 6 with the input unit 2. Various electrode arrangements are possible for a bioimpedance measurement. In FIG. 1 only 2 electrode elements 5a and 5b are connected to the bioimpedance measurement arrangement 5. Each of the electrode units 5a and 5b consists of a current-injecting electrode and of a potential-receiving electrode (not shown). Through the attaching of the two electrode units 5a and 5b to the wrist or to the ankle of a patient, as is sketched in FIG. 2(a), the whole body impedance of a patient can be determined in the usual manner, when no members or extremities are missing from the patient.

In addition, means 7 can be present for determining the height H(t) of the patient, the means being connected with the input unit 2 via a connection 8. The means 7 consist of a measurement device, as known in the prior art. In a further developed example embodiment of the invention, the means 7 also comprise weighing means for determining the weight M(t) of the patient.

In the example embodiment shown in FIG. 1, the input unit 2 contains an interface, via which the bioimpedance measurement values and the values for H(t) and M(t) are transferred directly via a connection 4 into the memory unit 3. It is likewise possible that the values or a part thereof are fed into the input unit 2 manually by a user.

Figure 4:
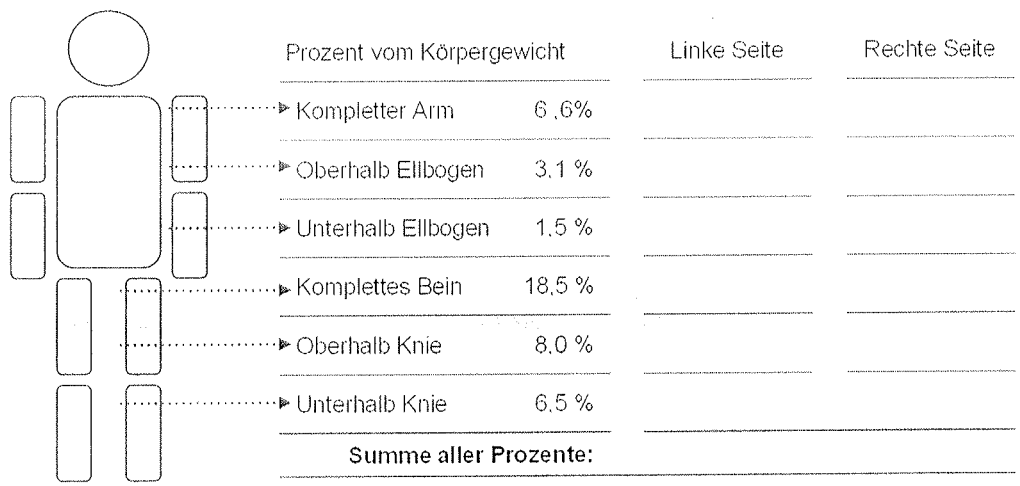

In the memory unit 3 in addition correction factors k are deposited in accordance with various degrees of amputation. These factors are determined in advance on the basis of comparative data which were obtained for patients who were not missing members or parts thereof. They can also be an integral component of the computer program deposited in the microprocessor program memory unit 1a. The correction factors can have been obtained from bioimpedance- or weight comparative measurements and be present for example simply in the form of percentage weight proportions. Such an example is shown in FIG. 4 for individual extremities such as complete arms and legs and also parts thereof. Here, if applicable, multiple amputations can be taken into consideration, by the individual proportions being added.

If it is possible, the factor k can also be determined individually by the weighing of the respective amputate of a patient compared with his total mass.

The device according to the invention for carrying out the method according to the invention proceeds as follows:

The user feeds in at the input unit 2 a selection of the degree of amputation of the patient. A previously deposited item of information can also be already stored in the memory unit 3, so that a new input is not necessary. In this case, the value deposited for the individual patient can be altered at any time via the input unit 2. It can also be the case that such items of information are imparted to the device 10 via a memory card by which a user logs the patient on to the device. Various solutions for this are familiar to the specialist in the art. The same applies for the transfer of the computer program into the microprocessor memory unit 1a. For this, the input unit 2 can have a corresponding interface for a computer program product, on which the computer program is stored. Numerous possibilities are also available to the specialist for this, such as CD- or DVD drives, USB interfaces, serial and parallel bus systems, bluetooth- or infrared interfaces, internet connection, various memory card reading systems etc.

The voltage- and current electrodes are attached to the patient according to the degree of amputation, for example in accordance with FIGS. 2(b)-(d), 3(a) or 3(b). A bioimpedance measurement is then initiated via the input unit 2 at the time 1, at which an electric current with one or with multiple frequencies is injected via the current electrodes and corresponding voltage values are measured. By means of the current- and voltage values, the bioimpedance measurement arrangement 5 can determine body impedance values of the patient which are made available via the memory unit 3 to the evaluation unit 1 for further evaluation. The evaluation unit 1 then determines the volume compartments of the extracellular water (ECW), of the intracellular water (ICW), of the overwatering volume (OH), of the lean tissue (LTM) and/or of the adipose tissue (ATM) with the aid of a patient model which does not initially take into consideration the degree of amputation of the patient. Such a method is shown for example in the already quoted international patent application WO 2006/002685, the disclosure of which is referred to in its entirety.

For the evaluation of the bioimpedance measurement data, the evaluation unit 1 takes into consideration a corrected body weight M'(t), which is produced from the body weight M(t) divided by the stored correction factor k:

$$M'(t)=M(t)/k \qquad (1).$$

This corrected body weight M'(t) now forms the basis of the determining of the volume compartments based on the evaluation programs hitherto, i.e. the evaluation takes place on the basis of a body weight of the patient, as if he has no members or extremities missing. The volume compartments of the extracellular water (ECW), of the intracellular water (ICW), of the overwatering volume (OH), of the lean tissue (LTM) and/or of the adipose tissue (ATM), now determined by the evaluation unit, are then transferred into the desired corrected volume compartments V(t) by multiplication with the correction factor k:

$$ECW(t)=k \cdot ECW'(t) \qquad (2a)$$

$$ICW(t)=k \cdot ICW'(t) \qquad (2b)$$

$$OH(t)=k \cdot OH'(t) \qquad (2c)$$

$$LTM(t)=k \cdot LTM' \qquad (2d)$$

$$ATM(t)=k \cdot ATM'(t) \qquad (2e).$$

The results are then passed on to an output unit 9 which is a display device and which displays the results to the user.

Further results—irrespective of whether they are intermediate results or outcome results—can be added to the informative image on the display.

The results for the corrected volume compartments can be stored in the device in order to make possible a trend analysis, which includes results derived at an earlier time. It has also proved to be useful to even out the data by a derivation of weighted average values from the last and the recent data. For this purpose, various algorithms are available in the prior art for the reduction of the statistical spread of the data. A useful improvement in the average calculation of the current results, which are displayed, was achieved by the ascribing of the highest weighting for the last measurement and by a reduction of the weighting of the other, earlier measurements with increasing time which has elapsed since these measurements.

Figure 3:
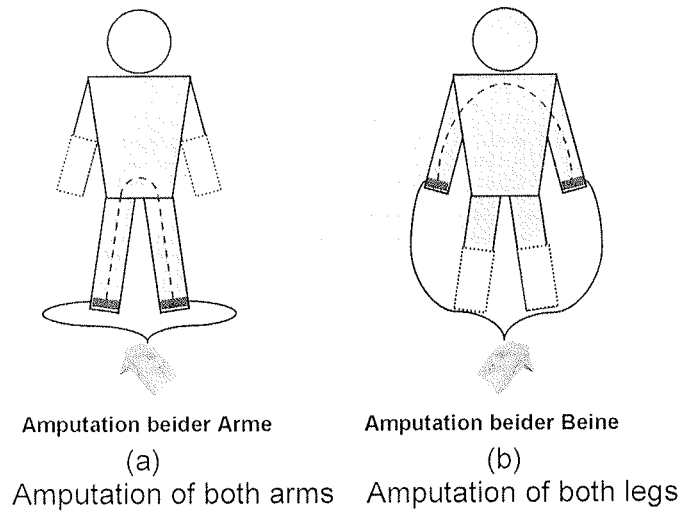

In the case of the amputation of both arms or both legs, a modification of the formulae can be necessary in accordance with the equations (2a)-(2e). In this case, an arrangement of the electrodes can be carried out as shown in FIG. 3. It has then proved to be expedient to correct the volume compartments by a correlated value in the following form:

$$ECW(t)=k \cdot (ECW'(t) \cdot m_{FF,HH} + o_{FF,HH}) \qquad (3a),$$

$$ICW(t)=k \cdot (ICW'(t) \cdot m_{FF,HH} + o_{FF,HH}) \qquad (3b),$$

$$OH(t)=k \cdot (OH')(t) \cdot m_{FF,HH} + o_{FF,HH}) \qquad (3c),$$

$$LTM(t)=k \cdot (LTM'(t) \cdot m_{FF,HH} + o_{FF,HH}) \qquad (3d),$$

$$ATM(t)=k \cdot (ATM'(t) \cdot m_{FF,HH} + o_{FF,HH}) \qquad (3e).$$

The index "FF" stands for the case where a measurement is carried out from foot to foot (FIG. 3(a)), the index "HH" where a measurement is carried out from hand to hand (FIG. 3(b)). Example values for corresponding factors m and offsets o are compiled in FIG. 5. These parameters can likewise be deposited in the memory unit 3. In the case of different measurement configurations, the device according to the invention can be further developed so that the user can select the measurement configuration via the input unit 2 (e.g. hand to foot, hand to hand or foot to foot), so that the evaluation unit 1 can take this into consideration in the evaluation.

By means of the invention, volume compartments can also be successfully determined in a simple manner in amputated patients by means of bioimpedance measurements, wherein the body models used and established hitherto for patients without amputations can be utilized without major adaptation. Merely the determining of a characteristic factor for the amputation is necessary, which can be determined by comparative measurements in advance. In particular exceptional situations of multiple amputations it can be indicated to submit additional parameters to increase accuracy. The previous body models can also be further used here for these circumstances.

Also understood as falling within the teaching according to the invention and therefore also within the claimed scope of protection are mathematically equivalent calculations in which measurement- or intermediate operands are replaced by proportional or other one-to-one correlated expressions. Such procedures likewise make use of the teaching according to the invention and are to be explicitly included in the framework of the terminology which is used.

The invention claimed is:

1. A method for determining a corrected volume compartment of an amputee patient at a time t, where the amputee patient is missing at least one individual member or parts thereof, the method comprising the following steps:

measuring the body weight of the amputee patient, calculating a corrected body weight based on a quotient resulting from dividing the measured body weight by a correction factor, which is characteristic of the at least one missing member or parts thereof, measuring bioimpedance data of the amputee patient at the time t, determining a volume compartment of the amputee patient based on the measured bioimpedance data, the corrected body weight, and a non-amputee patient model which does not initially take into consideration a degree of amputation of the amputee patient, and determining the corrected volume compartment by multiplying the volume compartment or a value correlated therewith with the correction factor.

2. The method according to claim 1, characterized in that the volume compartment is at least one selected from the following group: lean tissue (LTM), adipose tissue (ATM), overwatering volume (OH), extracellular water (ECW), intracellular water (ICW).

3. The method according to claim 1, characterized in that the bioimpedance measurement is a whole body measurement.

4. The method according to claim 3, characterized in that the whole body measurement is carried out by voltage and current electrodes, which, in the absence of an arm of parts thereof and/or in the absence of a leg or parts thereof, are attached in the vicinity of an existing wrist and in the vicinity of an existing ankle.

5. The method according to claim 3, characterized in that the whole body measurement is carried out by voltage and current electrodes, which, in the absence of both legs or parts of both legs, are attached in the vicinity of both wrists.

6. The method according to claim 3, characterized in that the whole body measurement is carried out by voltage and current electrodes, which, in the absence of both arms or parts of both arms, are attached in the vicinity of both ankles.

7. The method according to claim 1, characterized in that the correction factor is determined on the basis of comparative data, in which a proportion of the at least one missing member or of the parts thereof is determined on the basis of a proportion of the at least one missing member or of the parts thereof to the weight of a comparative non-amputee patient without a missing member or parts thereof.

8. A computer program product consisting of a memory storage medium containing a stored computer program executable on a computer to carry out the method according to claim 1.

9. A device for determining a corrected volume compartment of an amputee patient at a time (t), where the amputee patient is missing at least one individual member or parts thereof, comprising:

a bioimpedance measurement arrangement for the measurement of bioimpedance data on the patient, and an evaluation unit, which is configured for:
   calculating a corrected body weight based on a quotient resulting from dividing a measured body weight of the patient by a correction factor, which is characteristic of the at least one missing member or parts thereof,
   determining a volume compartment of the amputee patient based on the measured bioimpedance data, the corrected body weight, and a non-amputee patient model which does not initially take into consideration a degree of amputation of the patient, and
   determining the corrected volume compartment by multiplying the volume compartment or a value correlated therewith with the correction factor.

10. The device according to claim 9, characterized in that the volume compartment is at least one selected from the following group: lean tissue (LTM), adipose tissue (ATM), overwatering volume (OH), extracellular water (ECW), intracellular water (ICW).

11. The device according to claim 9, characterized in that the evaluation unit is further configured so that the bioimpedance measurement is evaluated as a whole body measurement.

12. The device according to claim 11, characterized in that the evaluation unit is configured to evaluate the whole body measurement when voltage and current electrodes are attached in the vicinity of an existing wrist and in the vicinity of an existing ankle in the absence of an arm or parts thereof and/or in the absence of a leg or parts thereof.

13. The device according to claim 11, characterized in that the evaluation unit is configured to evaluates the whole body measurement when voltage and current electrodes are attached in the vicinity of both wrists in the absence of both legs or parts of both legs.

14. The device according to claim 11, characterized in that the evaluation unit is configured to evaluates the whole body measurement when voltage and current electrodes are attached in the vicinity of both ankles in the absence of both arms or parts of both arms.

15. The device according to claim 9, characterized in that various correction factors for different degrees of amputation are stored in a memory unit and are able to be selected through an input unit.

16. The device according to claim 9, characterized in that said device further has an input unit for the input of the body weight of the amputee patient.

17. The device according to claim 16, characterized in that the input unit comprises an input apparatus for the manual input of the body weight of the amputee patient and/or a scales for the measurement and automatic communication of the measured body weight of the amputee patient.

18. A computer program product consisting of a memory storage medium containing a stored computer program executable by the evaluation unit of the device of claim 9 to cause to:
   calculate a corrected body weight based on a quotient resulting from dividing a measured body weight of the amputee patient by a correction factor, which is characteristic of the at least one missing member or parts thereof,
   determine a volume compartment of the amputee patient based on the measured bioimpedance data, the corrected body weight, and a non-amputee patient model which does not initially take into consideration a degree of amputation of the patient, and
   determine the corrected volume compartment by multiplying the volume compartment or a value correlated therewith with the correction factor.

* * * * *

UNITED STATES PATENT AND TRADEMARK OFFICE
CERTIFICATE OF CORRECTION

PATENT NO. : 8,583,226 B2  Page 1 of 1
APPLICATION NO. : 13/121039
DATED : November 12, 2013
INVENTOR(S) : Moissl et al.

It is certified that error appears in the above-identified patent and that said Letters Patent is hereby corrected as shown below:

In the Claims

In claim 13, column 8, line 23, change "evaluates" to --evaluate--;

In claim 14, column 8, line 28, change "evaluates" to --evaluate--.

Signed and Sealed this
Fifteenth Day of April, 2014

Michelle K. Lee
*Deputy Director of the United States Patent and Trademark Office*